United States Patent
Utsumi et al.

(10) Patent No.: US 9,281,157 B2
(45) Date of Patent: Mar. 8, 2016

(54) RADIATION GENERATING APPARATUS AND RADIOGRAPHY SYSTEM INCLUDING THE RADIATION GENERATING APPARATUS

(71) Applicant: CANON KABUSHIKI KAISHA, Tokyo (JP)

(72) Inventors: Kazushige Utsumi, Sagamihara (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/171,452

(22) Filed: Feb. 3, 2014

(65) Prior Publication Data
US 2014/0226787 A1    Aug. 14, 2014

(30) Foreign Application Priority Data

Feb. 13, 2013    (JP) ................................ 2013-025729

(51) Int. Cl.
*H05G 1/02* (2006.01)
*H01J 35/08* (2006.01)
*H01J 35/12* (2006.01)
*H01J 35/06* (2006.01)
(Continued)

(52) U.S. Cl.
CPC . *H01J 35/08* (2013.01); *A61B 6/40* (2013.01); *H01J 35/065* (2013.01); *H01J 35/12* (2013.01); *H01J 35/16* (2013.01); *H05G 1/025* (2013.01); *H01J 2235/068* (2013.01); *H01J 2235/087* (2013.01); *H01J 2235/1204* (2013.01); *H01J 2235/1291* (2013.01); *H01J 2235/168* (2013.01); *H01J 2235/186* (2013.01)

(58) Field of Classification Search
CPC . H01J 35/10; H01J 35/108; H01J 2235/1204; H01J 2235/1229; H01J 35/08; H01J 35/12; H01J 35/18; H01J 2235/08; H01J 2235/083; H01J 2235/086; H01J 2235/087; H01J 2235/12; H01J 2235/1291; H01J 2235/1295; H01J 2235/18; H01J 2235/186; A61B 6/4007; A61B 6/4021; H05G 1/02; H05G 1/025
USPC .......................... 378/119, 121, 122, 136, 139
See application file for complete search history.

(56) References Cited

U.S. PATENT DOCUMENTS

| 6,850,598 | B1 | 2/2005 | Fryda et al. |
| 2003/0021377 | A1 | 1/2003 | Turner et al. |
| 2009/0232270 | A1* | 9/2009 | Okunuki et al. .................. 378/5 |

(Continued)

FOREIGN PATENT DOCUMENTS

| CN | 101395691 A | 3/2009 |
| CN | 101521136 A | 9/2009 |

(Continued)

*Primary Examiner* — Thomas R Artman
(74) *Attorney, Agent, or Firm* — Canon USA Inc. IP Division

(57) ABSTRACT

A radiation generating apparatus includes a cathode array including a plurality of electron emitting portions, and an anode array including a plurality of targets and a chained connection unit that connects the targets. The chained connection unit includes a plurality of shielding members and a thermal transfer member, the shielding members being arranged at locations corresponding to the locations of the respective targets, and the thermal transfer member having a thermal conductivity higher than a thermal conductivity of the shielding members. The thermal transfer member has a portion that is continuous in a direction in which the targets are arranged.

54 Claims, 8 Drawing Sheets

(51) Int. Cl.
*H01J 35/16* (2006.01)
*A61B 6/00* (2006.01)

(56) References Cited

U.S. PATENT DOCUMENTS

2009/0316860 A1* 12/2009 Okunuki et al. ............. 378/122
2012/0318987 A1 12/2012 Miyazaki et al.
2014/0140486 A1* 5/2014 Yanagisawa et al. ......... 378/141

FOREIGN PATENT DOCUMENTS

| | | |
|---|---|---|
| CN | 102792782 A | 11/2012 |
| JP | 2007265981 A | 10/2007 |
| JP | 2009545840 A | 12/2009 |
| WO | 2012/077463 A1 | 6/2012 |

* cited by examiner

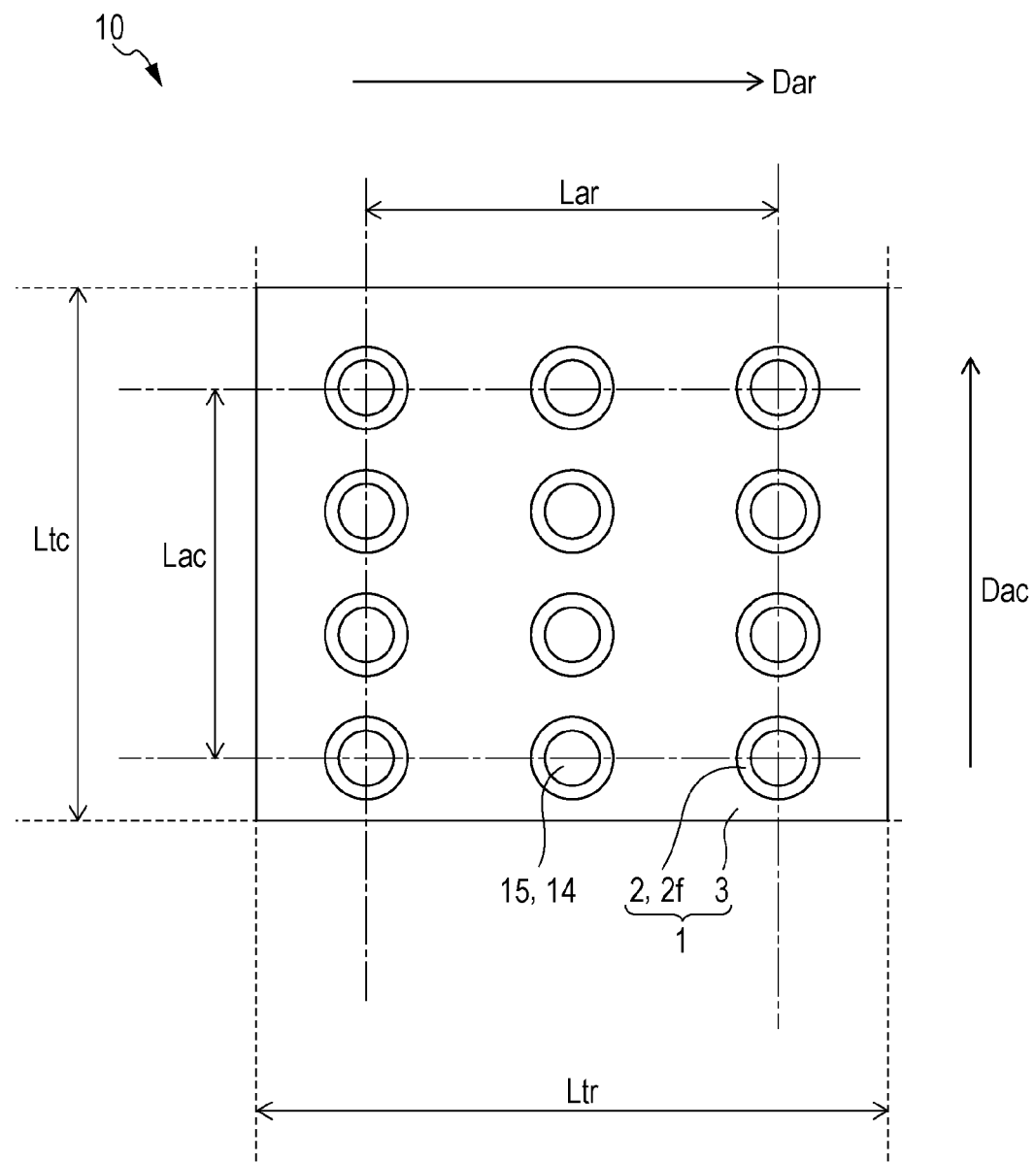

RADIATION GENERATING APPARATUS AND RADIOGRAPHY SYSTEM INCLUDING THE RADIATION GENERATING APPARATUS

BACKGROUND OF THE INVENTION

1. Field of the Invention

The present invention relates to radiation generating apparatuses for, in particular, diagnostic application in the field of medical equipment and nondestructive radiography in the field of industrial equipment.

2. Description of the Related Art

Radiation generating apparatuses that generate X-rays for use in medical diagnosis and industrial non-destructive imaging are required to have a high durability and maintenance efficiency to increase the operating rate thereof. Such a radiation generating apparatus may serve as a portable medical modality applicable to home medical care or emergency medical care in case of, for example, a disaster or an accident.

The thermal stability of a target that serves as a source of radiation is one of the main factors that determine the durability of the radiation generating apparatus.

In the radiation generating apparatus, which generates radiation by irradiating the target with electron beams, the "radiation generation efficiency" of the target is less than 1% because most of the energy supplied by the electron beams to the target is converted into heat. When dissipation of the heat generated by the target is not sufficient, a problem occurs in that the adhesion of the target to its support member is reduced due to thermal stress, and the thermal stability of the target is limited.

A known method for increasing the "radiation generation efficiency" of the target is to use a transmissive target including a thin-film-shaped target layer, which contains a heavy metal, and a support member, which allows the radiation to pass therethrough and supports the target layer. PCT Japanese Translation Patent Publication No. 2009-545840 discloses a rotating-anode transmissive target with which the "radiation generation efficiency" is increased to 1.5 times that of a known rotating-anode reflective target.

A known method for promoting the dissipation of heat from the target to the outside is to use diamond as the material of the support member that supports the target layer of the multilayer target. U.S. Pat. No. 6,850,598 discloses that the heat dissipation effect can be increased and the focal spot size can be reduced when the support member that supports the target layer, which is made of tungsten, is made of diamond. Diamond has high radiotransparency as well as high thermal stability and thermal conductivity, and is therefore suitable as a material of a support member of a transmissive target.

With the development of image processing technologies, such as tomography, for medical diagnosis, array-type radiation generating apparatuses that emit a plurality of X-ray beams have been developed as a modality. Such an array-type radiation generating apparatus includes radiation generating units arranged in an array, and each radiation generating unit is configured to be individually controllable.

Japanese Patent Laid-Open No. 2007-265981 discloses a structure of an array-type radiation generating apparatus in which shielding members having openings are provided on front and back sides of a plate-shaped target including a plurality of radiation generating units. The plate-shaped target is thermally in contact with the shielding members. Owing to this structure, according to Japanese Patent Laid-Open No. 2007-265981, a plurality of X-ray beams with regulated radiation angles are emitted toward the front of the radiation generating apparatus, and the heat of the target can be radiated through the shielding member on the front side of the target.

SUMMARY OF THE INVENTION

In an array-type radiation generating apparatus including a plurality of shielding members for respective targets, reduction in the stability of the radiation output has been observed. The observed reduction in stability of the radiation output, that is, radiation output variation, was more prominent in a central region than in a peripheral region of the array.

As a reference example, FIGS. 7A to 7C show a schematic structure of an anode array 40 in which a radiation output variation was observed in a central region of an array including a plurality of targets. FIG. 7A is a plan view of the anode array viewed from an opening side from which the radiation is emitted. FIGS. 7B and 7C are sectional views of the anode array illustrated in FIG. 7A taken along imaginary lines VIIB-VIIB and VIIC-VIIC, respectively.

In this reference example, three multilayer targets 15, each target 15 including a target layer 13 and a support member 14, are arranged in an arrangement direction Dat at a pitch of ½×Lat, so that the arrangement length is Lat. The anode array 40 is formed by connecting the targets 15 with a chained connection unit 41 including shielding members 42 and thermal transfer members 43.

Each shielding member 42 is a rectangular-parallelepiped-shaped block made of tungsten, and has a columnar opening that opens at two opposing faces of the block. The inner wall of the opening in each shielding member 42 is connected to a side surface of the corresponding target 15 with a solder material (not shown) interposed therebetween. The thermal transfer members 43 are made of a material having a thermal conductivity higher than that of the shielding members 42.

In this reference example, the shielding members 42 are disposed between the thermal transfer members 43, and are arranged discontinuously in the arrangement direction Dat of the anode array 40 in the chained connection unit 41. In this reference example, the length Ltt of each thermal transfer member 43 is smaller than the arrangement length Lat of the targets 15, and is also smaller than the array pitch ½×Lat of the targets 15. The thermal transfer members 43 are discretely arranged in the anode array 40.

As a result of diligent studies conducted by the inventors of the present invention, it has been found that the variation in the radiation output from the array-type radiation generating apparatus according to the reference example is caused by the thermal resistance of the anode array 40, which includes the plurality of targets 15, in the arrangement direction Dat of the anode array 40.

More specifically, the inventors of the present invention have found that the shielding members 42 serve as bottlenecks of heat conduction in the arrangement direction Dat of the anode array 40 and hinder the effective radiation of the heat generated by the target 15 at the center of the array.

The reduction in the radiation output stability causes non-uniform radiation output in the arrangement direction of the array, and leads to a limitation to the anode current that can be supplied to the targets and a limitation to the level to which the output of the radiation generating apparatus can be increased. Therefore, there has been a demand to suppress the reduction in the radiation output stability.

Accordingly, the present invention provides a reliable radiation generating apparatus which is an array-type radiation generating apparatus including a plurality of shielding members for respective targets and in which the radiation output variation due to the reduction in heat conduction in the arrangement direction of the array is suppressed. The present invention also provides a radiography system.

A radiation generating apparatus according to an aspect of the present invention includes a cathode array including a plurality of electron emitting portions, and an anode array including a plurality of targets and a chained connection unit that connects the targets, the targets being arranged at locations corresponding to locations of the respective electron emitting portions and generating radiation when irradiated with electrons emitted from the respective electron emitting portions. The chained connection unit includes a plurality of shielding members and a thermal transfer member, the shielding members being arranged at locations corresponding to the locations of the respective targets, the thermal transfer member having a thermal conductivity higher than a thermal conductivity of the shielding members. The thermal transfer member extends continuously in a direction in which the targets are arranged.

Further features of the present invention will become apparent from the following description of exemplary embodiments with reference to the attached drawings.

BRIEF DESCRIPTION OF THE DRAWINGS

FIG. 5 is a plan view of another example of an anode array applicable to a radiation generating apparatus according to an embodiment of the present invention.

DESCRIPTION OF THE EMBODIMENTS

A radiation generating apparatus and a radiography system according to embodiments of the present invention will now be described with reference to the drawings. Materials, dimensions, shapes, relative arrangement, etc., of components described in the embodiments are not intended to limit the scope of the present invention unless otherwise stated.

Radiation Generating Apparatus

Figure 2A:
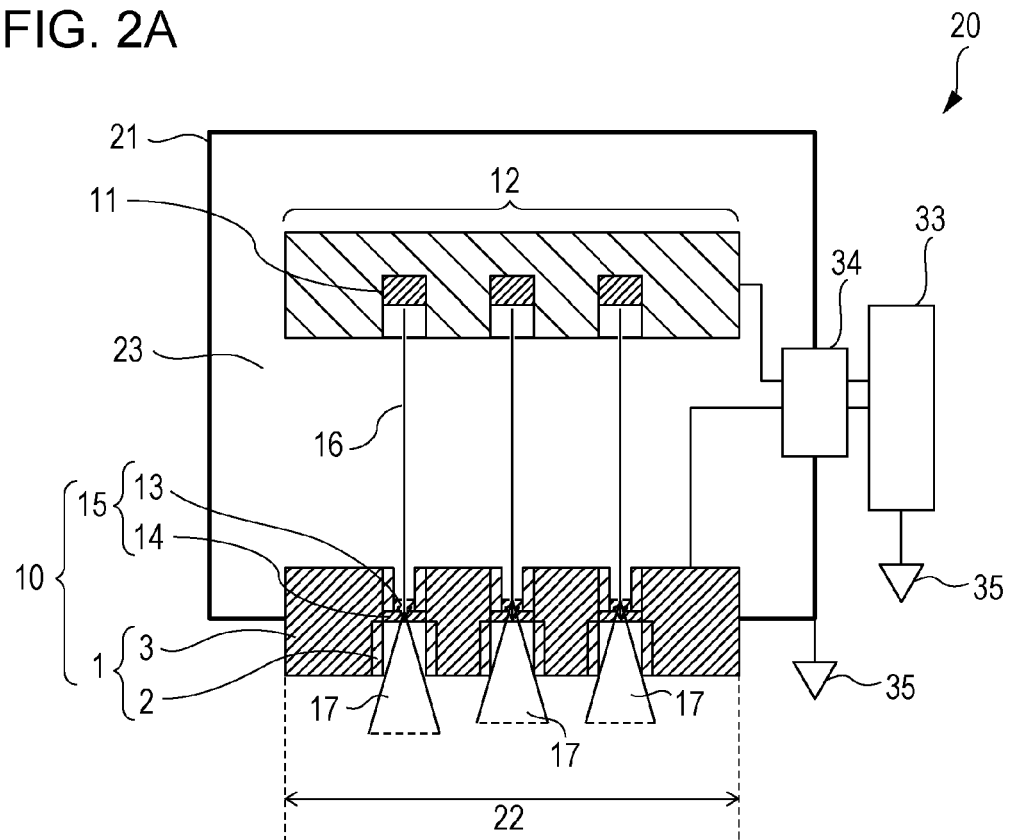
FIGS. 2A and 2B are a sectional view and a plan view, respectively, of a radiation generating apparatus according to an embodiment of the present invention.
Figure 2B:
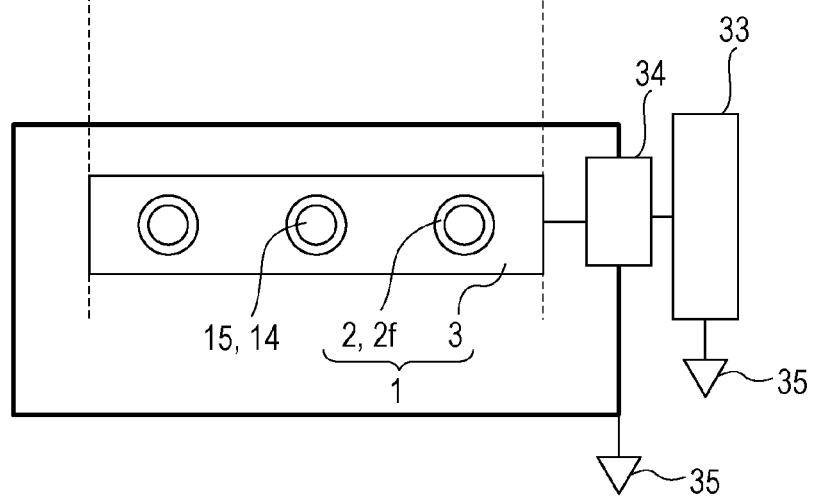

First, a basic structure of a radiation generating apparatus according to an embodiment of the present invention will be described with reference to FIGS. 2A, 2B, and 8. FIG. 2A is a schematic sectional view of a radiation generating apparatus 20 including a drive circuit 33. FIG. 2B is a plan view of the radiation generating apparatus 20 illustrated in FIG. 2A viewed from the side at which an anode array 10 is arranged.

In the present embodiment, as illustrated in FIG. 2A, the radiation generating apparatus 20 includes a cathode array 12 including a plurality of electron emitting portions 11. The radiation generating apparatus 20 according to the present embodiment also includes an anode array 10 including a plurality of targets 15, which are arranged at locations corresponding to the locations of the respective electron emitting portions 11, and a chained connection unit 1, which connects the targets 15 to each other.

The chained connection unit 1 includes shielding members 2 arranged at locations corresponding to the locations of the targets 15 and a thermal transfer member 3 having a thermal conductivity higher than that of the shielding members 2. The thermal transfer member 3 is formed so as to extend continuously in an arrangement direction Dat in which the targets 15 are arranged. The chained connection unit 1 will be described in detail later.

In the present embodiment, as illustrated in FIGS. 2A and 2B, an envelope 21, which is a container made of brass, is provided. The cathode array 12 is disposed in an inner area 23 of the envelope 21, and the anode array 10 is connected to an opening 22 in the envelope 21 so that target layers 13 face the respective electron emitting portions 11.

In the present embodiment, the cathode array 12 and the anode array 10 are connected to the drive circuit 33, which defines a cathode potential and an anode potential, through a current introduction terminal 34. The anode array 10 is connected to a ground terminal 35 together with the envelope 21. In other words, in the radiation generating apparatus 20 according to the present embodiment, anodes are grounded.

The type of the electron emitting portions 11 is not particularly limited as long as the electron emitting portions 11 can be controlled by the drive circuit 33. Electron sources included in the electron emitting portions 11 may either be cold cathodes or hot cathodes. Carbon nanotube (CNT) cathodes, impregnated electron guns, etc., may be used as the electron sources.

The envelope 21 is a container that allows the electron emitting portions 11 and the target layers 13 to be arranged in the inner area 23 thereof or on the inner surface thereof.

To ensure sufficient mean free path of electrons and sufficient life of the electron emission characteristics of the electron emitting portions 11, the inner area 23 of the envelope 21 is evacuated to vacuum. To achieve these purposes, the vacuum in the inner area 23 of the envelope 21 can be $1 \times 10^{-4}$ Pa or more and $1 \times 10^{-8}$ Pa or less.

Accordingly, the envelope 21 can be strong enough to withstand the atmospheric pressure. Since the anode array 10 according to the present embodiment constitutes a part of the envelope 21, the anode array 10 can also be strong enough to withstand the atmospheric pressure.

In the present embodiment, since the anode array 10 is connected to the envelope 21, the anode array 10 provides a function of increasing the apparatus strength due to the physical connection, an apparatus driving function due to the electrical connection, and a radiation promoting function due to the conductive connection.

Radiography System

Figure 8:
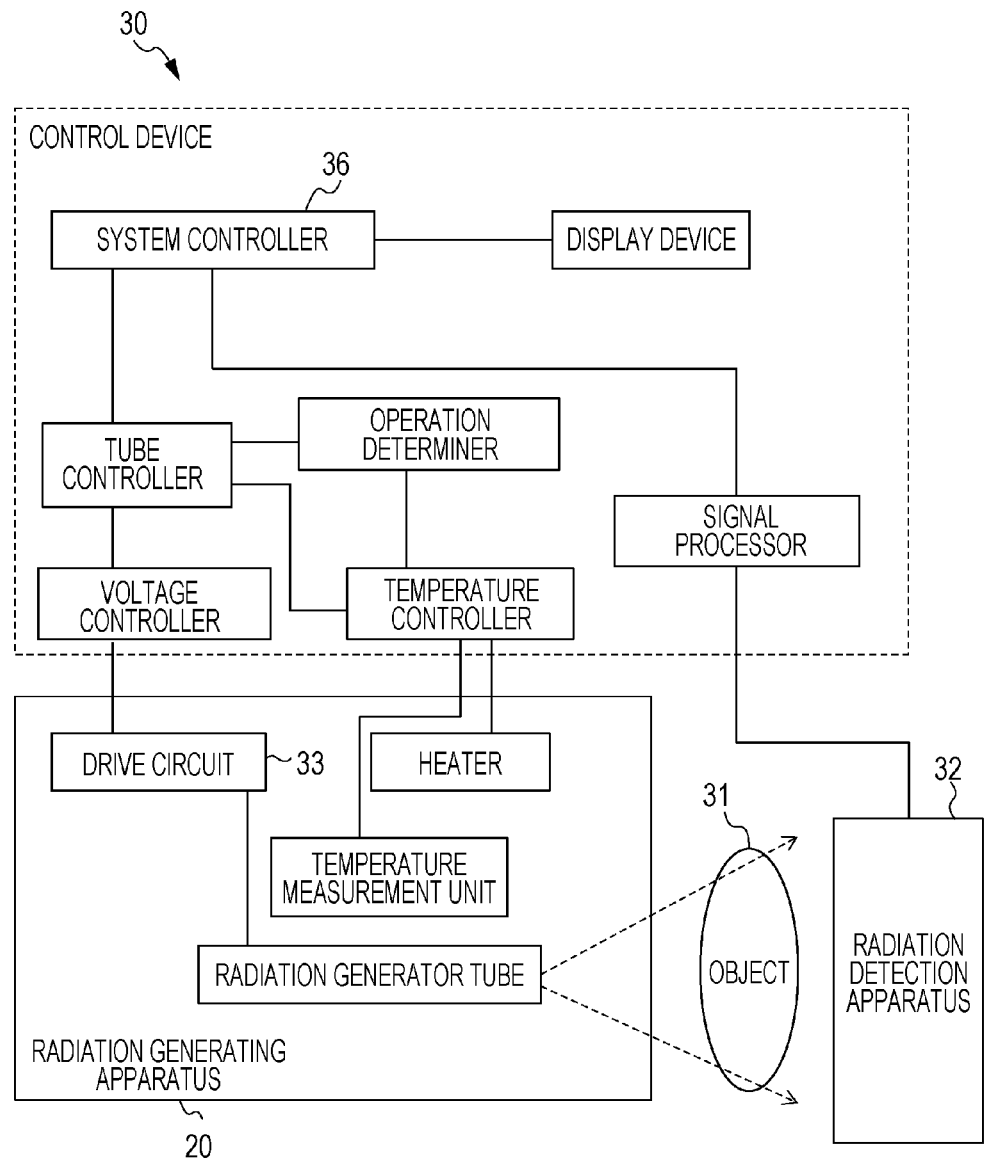
FIG. 8 illustrates a radiography system including the radiation generating apparatus according to the embodiment of the present invention.

Referring to FIG. 8, the radiation generating apparatus 20 according to the embodiment of the present invention may be included in a radiography system 30. The radiography system 30 includes a radiation detection apparatus 32 that detects radiation 17 (in FIG. 2A) emitted from the radiation generating apparatus 20 and transmitted through an object 31, and a system controller 36 which controls the radiation generating apparatus 20 and the radiation detection apparatus 32 in association with each other.

Anode Array

An example of the anode array 10 applicable to the radiation generating apparatus according to an embodiment of the present invention will now be described with reference to FIGS. 1A to 1C. The anode array 10 is a characteristic component according to an embodiment of the present invention.

Figure 1A:
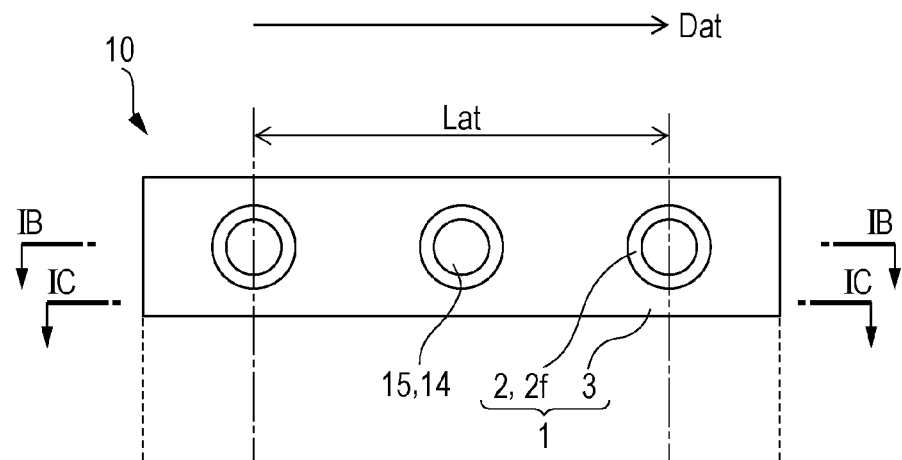
FIG. 1A is a plan view of a basic example of an anode array applicable to a radiation generating apparatus according to an embodiment of the present invention.

FIG. 1A is a plan view of the anode array 10 viewed from the side at which openings for emitting the radiation 17 (in FIG. 2A) are formed. FIGS. 1B and 1C are sectional views of the anode array 10 illustrated in FIG. 1A taken along imaginary lines IB-IB and IC-IC, respectively.

Each target 15 of this example is a multilayer target including a target layer 13 and a support member 14 that supports the target layer 13.

Each multilayer target 15 includes the target layer 13 formed on one side of the support member 14. The method for forming the target layers 13 is not particularly limited; for example, sputtering, vapor deposition, pulse-laser deposition, or a gas-phase film forming method such as chemical vapor deposition (CVD) may be used.

The target layers 13 are thin films containing a target metal. The metal used as the target metal may be selected as appropriate in accordance with the required radiation quality and acceleration voltage between the anode and the cathode, and a metallic element having an atomic number of 40 or more, such as tungsten, molybdenum, or tantalum, is selected.

The target layers 13 are not limited to those containing the target metal as a pure metal, and the target metal may be contained in the form of a metallic alloy, nitride, carbide, or oxide.

The support members 14 can be made of a material that is resistant to the operating temperature of the radiation generating apparatus or the temperature during manufacture of the radiation generating apparatus. For example, beryllium, graphite, or diamond may be used. From the viewpoint of thermal stability, thermal conductivity, and self-attenuation of radiation, the support members 14 can be made of diamond.

When each target 15 has a multilayer structure as described above, the functions of radiation generation, heat dissipation, and suppression of self-attenuation of radiation 17 can be separately provided and the materials of the components can be optimized.

In the case where diamond is used as the material of the support members 14, from the viewpoint of manufacturing process and material cost, it is not practical to form an anode array including a single plate-shaped support member as described in Japanese Patent Laid-Open No. 2007-265981. Therefore, in the case where diamond is used as the material of the support members 14 of the anode array, it is practical to discretely arrange the support members 14 made of diamond and connect the adjacent support members 14 made of diamond with the chained connection unit 1, as illustrated in FIG. 1A to 1C.

Thus, an array-type radiation generating apparatus according to an embodiment of the present invention is a radiation generating apparatus including an anode array that includes a plurality of multilayer targets and a chained connection unit connecting the multilayer targets, the chained connection unit including shielding members that correspond to the respective targets.

Next, the chained connection unit 1, which is a characteristic component of the anode array 10 according to the present embodiment, will be described. The chained connection unit 1 includes the shielding members 2 and the thermal transfer member 3.

Figure 1B:
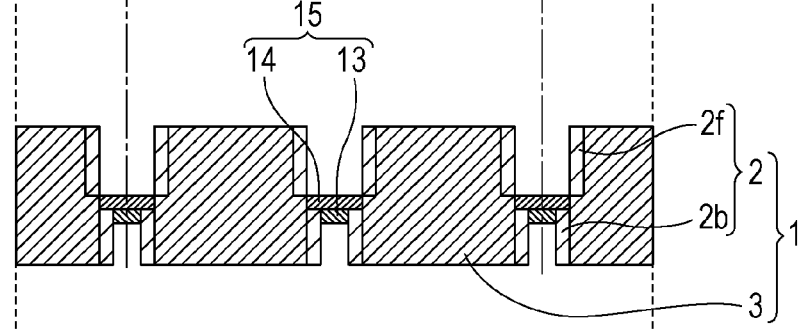
FIGS. 1B and 1C are sectional views of FIG. 1A taken along lines IB-IB and IC-IC, respectively.

As illustrated in FIG. 1B, which is a sectional view taken along line IB-IB that passes through the central axis along which the targets 15 are arranged, the thermal transfer member 3 of the anode array 10 is divided into discontinuous portions by the shielding members 2 that correspond to the targets 15. However, as illustrated in FIGS. 1A and 1C, the thermal transfer member 3 has a length Ltt and extends continuously over a range greater than the arrangement length Lat of the targets 15 in the arrangement direction Dat of the targets 15.

The heat transfer mechanism of this structure is represented by an equivalent circuit in which three heat sources are connected in parallel to a serial heat transfer path of the thermal transfer member 3 via thermal resistances of the support members 14 at locations separated from each other by intervals of ½×Lat.

Figure 7A:
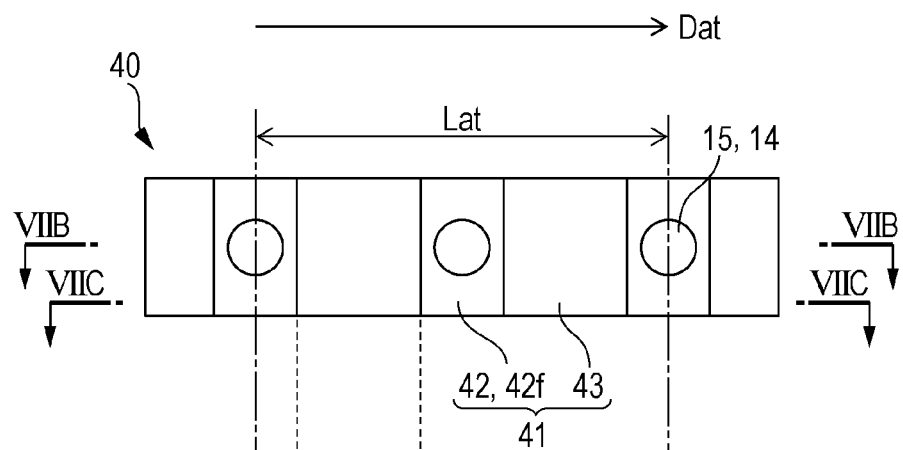
FIG. 7A is a plan view of an anode array according to a reference example in which a variation in radiation intensity was observed in a central area of the anode array.
Figure 7B:
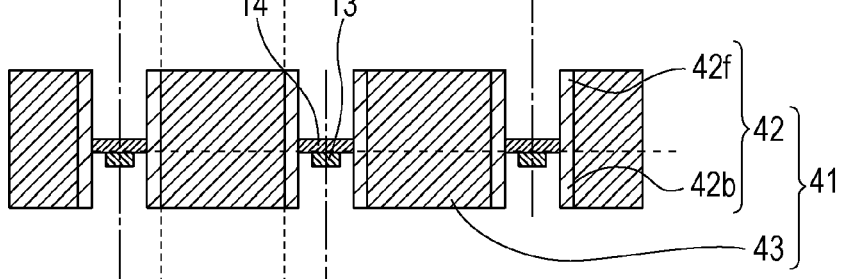
FIGS. 7B and 7C are sectional views of FIG. 7A taken along lines VIIB-VIIB and VIIC-VIIC, respectively.
Figure 7C:
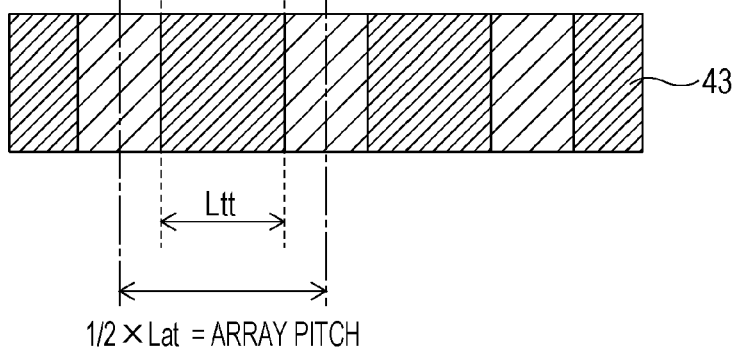

In this example, no shielding members having a large thermal resistance are arranged so as to impede the heat transfer in the arrangement direction Dat of the targets 15 and the direction opposite to the arrangement direction Dat. Therefore, the heat emitted from the target 15 at the center of the arrangement is effectively transferred to the ends of the arrangement. This is the difference between the anode array 10 of this example and the anode array 40 illustrated in FIGS. 7A to 7C in which a radiation output variation was observed.

Each shielding member 2 may be composed of a back shielding portion 2b arranged on a side of the corresponding target layer 13 that faces the corresponding electron emitting portion 11, and a front shielding portion 2f arranged on a side of the target layer 13 that is opposite to the side facing the electron emitting portion 11.

With regard to the material of the shielding members 2, a material having a high specific gravity may be selected as appropriate in consideration of the quality and intensity of the radiation generated by the target layers 13. To achieve a good balance between the radiation shielding performance and cost, the material can contain tungsten (specific gravity is 19000 $kg/m^3$ and thermal conductivity is 115 W/m/K at 1200K) as a main component.

In the case where each shielding member 2 includes the back shielding portion 2b, the target metal contained in the target layers 13 may be used as the material of the shielding members 2. In such a case, the influence of degradation of radiation quality caused by electrons reflected by the target layers 13 can be reduced.

According to an embodiment of the present invention, the shielding members 2 are made of a material having a specific gravity higher than that of the thermal transfer member 3. Accordingly, the radiation shielding performance can be provided separately from the heat dissipation performance provided by the thermal transfer member 3. This contributes to increasing the thermal resistance of the anode array 10 and reducing the size of the anode array 10.

The thermal transfer member 3 is made of a material having a thermal conductivity higher than that of the shielding members 2. To achieve a good balance between the thermal conductivity and cost, the material can contain copper (specific gravity is 8460 $kg/m^3$ and thermal conductivity is 342

W/m/K at 1200 K), silver (specific gravity is 9824 kg/m³ and thermal conductivity is 358 W/m/K at 1200 K), or an alloy thereof as a main component.

Figure 6A:
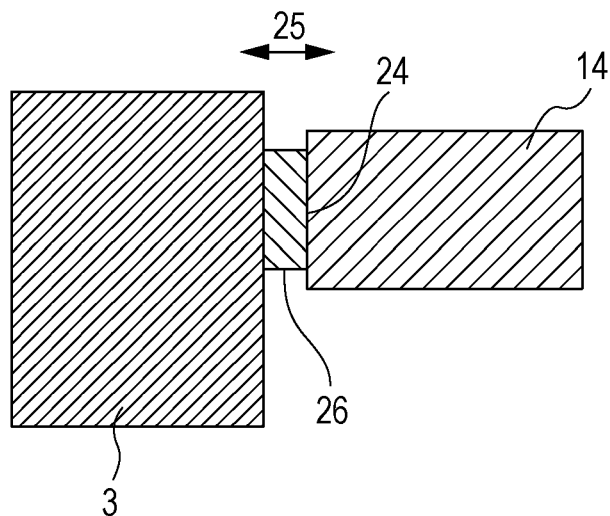
FIGS. 6A and 6B are enlarged views of connecting portions between targets and chained connection units in the examples illustrated in FIGS. 1A to 1C and 3A to 3C, respectively.

FIG. 6A is an enlarged view of a connecting portion between each support member 14 and the chained connection unit 1 illustrated in FIG. 1A. FIG. 6A shows a solder material 26 that is not illustrated in FIG. 1A. As illustrated in FIG. 6A, the anode array 10 of this example includes a connecting portion 25 which couples the thermal transfer member 3 to the side surface of the support member 14 with the solder material 26 interposed therebetween.

When the solder material 26 is made of silver solder, the thermal conductivity thereof can be made higher than that of the shielding members 2 (about 150 to 200 W/m/K). Unlike the shielding members 2, the solder material 26 occupies very small spaces in the chained connection unit 1, so that the continuity of the thermal transfer member 3 is not reduced even when the solder material 26 is arranged as illustrated in FIG. 6A.

OTHER EXAMPLES

Other examples of the anode array 10 applicable to a radiation generating apparatus according to an embodiment of the present invention will be described with reference to FIGS. 3A to 3C, 4A to 4C, 5, 6A, and 6B.

Figure 1C:
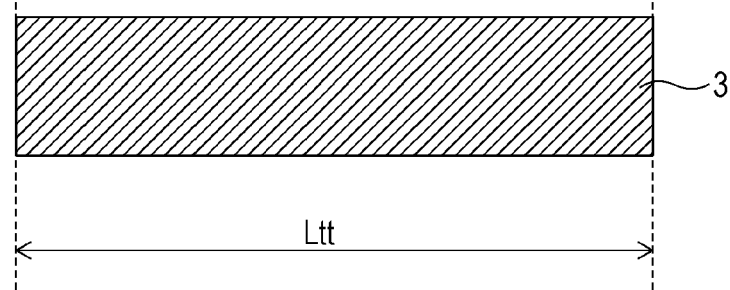
Figure 3A:
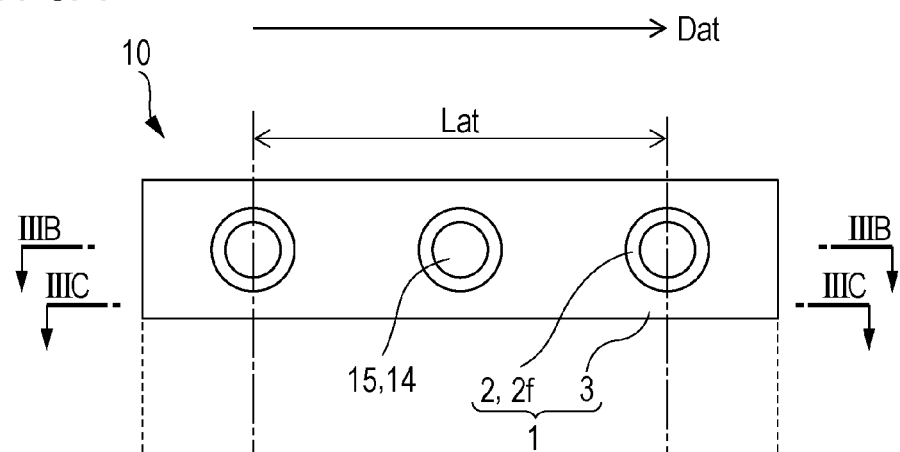
FIG. 3A is a plan view of another example of an anode array applicable to a radiation generating apparatus according to an embodiment of the present invention.
Figure 3B:
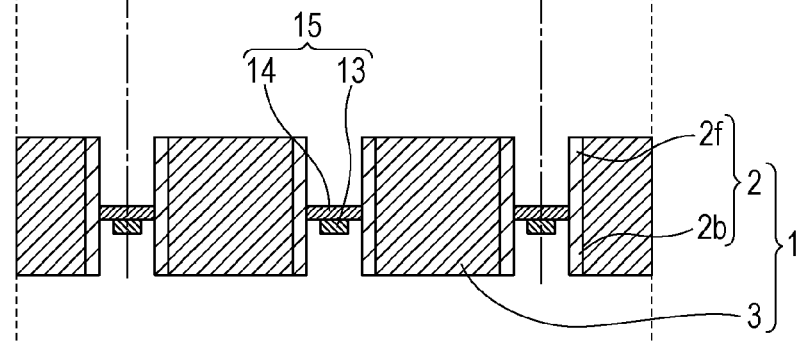
FIGS. 3B and 3C are sectional views of FIG. 3A taken along lines IIIB-IIIB and IIIC-IIIC, respectively.
Figure 3C:
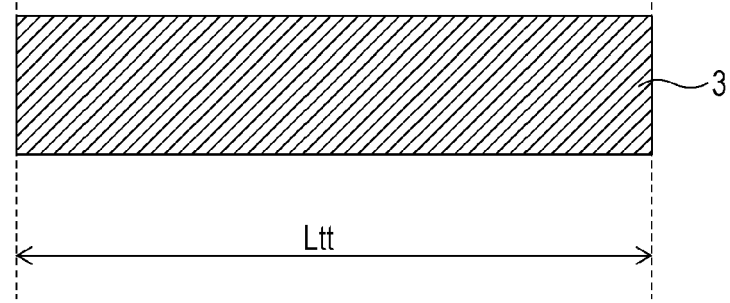
Figure 6B:
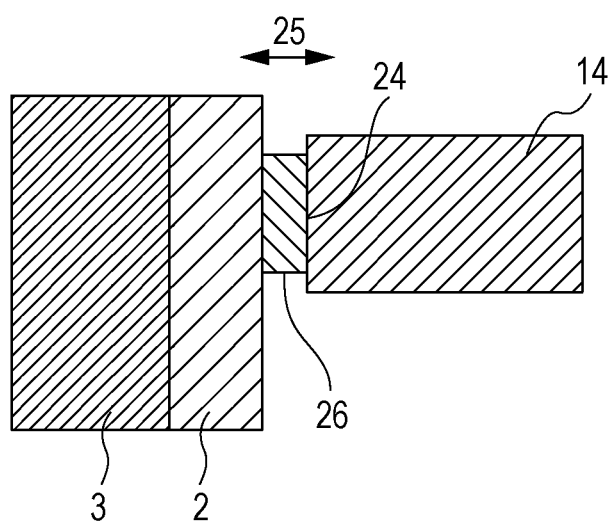

In an anode array 10 illustrated in FIGS. 3A to 3C, the manner in which a support member 14 of each target 15 is coupled to a chained connection unit 1 differs from that in the anode array 10 illustrated in FIGS. 1A to 1C. FIG. 6B is an enlarged view of a connecting portion between each support member 14 and the chained connection unit 1 illustrated in FIG. 3B. FIG. 6B shows a solder material 26 that is not illustrated in FIG. 3A.

As illustrated in FIG. 6B, the anode array 10 of this example includes a connecting portion 25 which couples the thermal transfer member 3 to the side surface of the support member 14 with the solder material 26 and the shielding member 2 interposed therebetween. This connecting portion 25 differs from the connecting portion 25 illustrated in FIG. 6A in that the shielding member 2 is interposed between the thermal transfer member 3 and the side surface of the support member 14.

FIGS. 3B and 3C are sectional views of the anode array 10 illustrated in a plan view of FIG. 3A, taken along imaginary lines IIIB-IIIB and IIIC-IIIC, respectively.

The heat transfer mechanism of this structure is represented by an equivalent circuit in which three heat sources are connected in parallel to a serial heat transfer path of the thermal transfer member 3 via serial thermal resistances of the support members 14 and the shielding member 2 at locations separated from each other by intervals of ½×Lat.

This heat transfer mechanism differs from that of the anode array 10 illustrated in FIGS. 1A to 1C in that thermal resistances of the shielding members 2 are provided in heat transfer paths that connect the heat sources in parallel to the serial heat transfer path of the thermal transfer member 3 at three locations. Accordingly, the heat dissipation performance of the anode array 10 of this example is relatively low. However, also in the anode array 10 of this example, as illustrated in FIGS. 3A and 3C, the thermal transfer member 3 has a length Ltt and extends continuously over a range greater than the arrangement length Lat of the targets 15 in the arrangement direction Dat of the targets 15. Thus, this anode array 10 also has the characteristic feature according to an embodiment of the present invention.

Figure 4A:
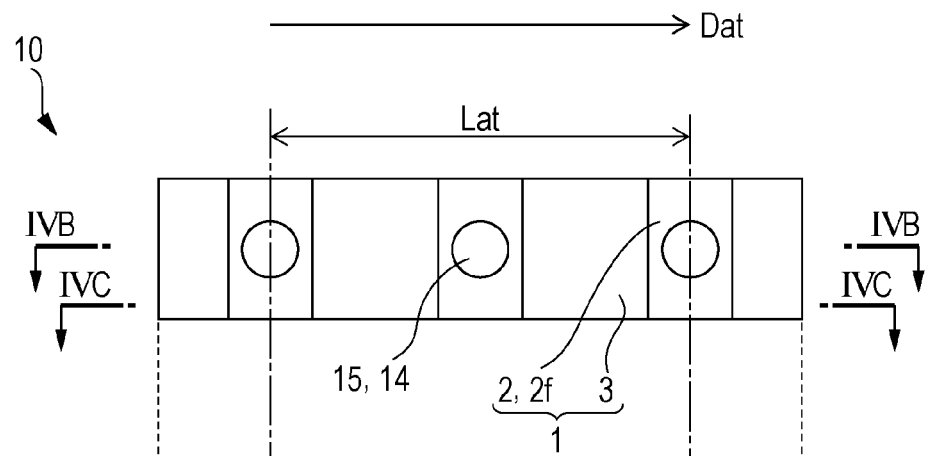
FIG. 4A is a plan view of another example of an anode array applicable to a radiation generating apparatus according to an embodiment of the present invention.
Figure 4B:
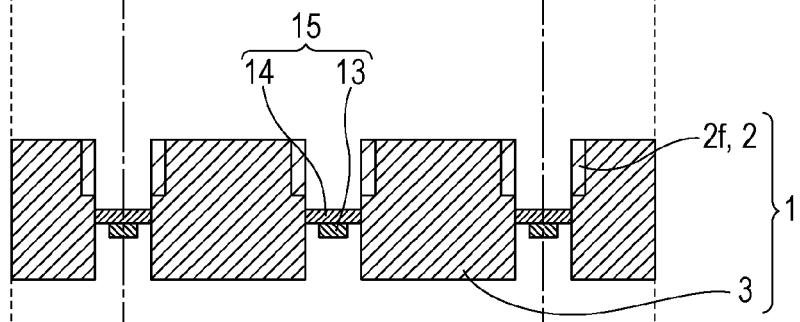
FIGS. 4B and 4C are sectional views of FIG. 4A taken along lines IVB-IVB and IVC-IVC, respectively.
Figure 4C:
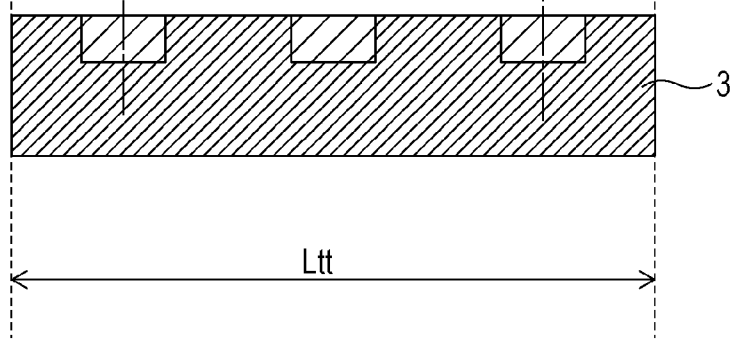

In an anode array 10 illustrated in FIGS. 4A to 4C, a region in which each shielding member 2 is formed differs from that in the anode array 10 illustrated in FIGS. 1A to 1C. FIGS. 4B and 4C are sectional views of the anode array 10 illustrated in a plan view of FIG. 4A, taken along imaginary lines IVB-IVB and IVC-IVC, respectively.

The heat transfer mechanism of this structure is represented by an equivalent circuit in which three heat sources are connected in parallel to a serial heat transfer path of the thermal transfer member 3 via thermal resistances of the support members 14 at locations separated from each other by intervals of ½×Lat. The anode array 10 of this example has a heat dissipation performance equivalent to that of the anode array 10 illustrated in FIGS. 1A to 1C.

FIG. 5 illustrates an anode array 10 whose array pattern differs from that of the anode array 10 illustrated in FIGS. 1A to 1C. The anode array 10 illustrated in FIGS. 1A to 1C has a one-dimensional arrangement pattern, while the anode array 10 of this example illustrated in FIG. 5 has a two-dimensional arrangement pattern. Also in this example, the thermal transfer member 3 has lengths Ltr and Ltc and extends continuously over ranges greater than the arrangement lengths Lar and Lac in the arrangement directions Dar (row direction) and Dac (column direction).

Thus, the arrangement pattern of the targets included in the anode array applied to a radiation generating apparatus according to an embodiment of the present invention is not limited to a one-dimensional arrangement pattern. In addition, with regard to the arrangement direction, the targets are not necessarily arranged along orthogonal lines of a matrix or along a straight line, and the present invention may be applied to anode arrays having other arbitrary arrangement patterns.

Example 1

An anode array 10 having the structure illustrated in FIGS. 1A to 1C was manufactured by the following processes.

That is, first, disc-shaped support members 14 having a thickness of 1 mm and a diameter of 6 mm and made of diamond were prepared. Next, the support members 14 were subjected to degreasing using an organic solvent, and residual organic substances were removed by using an ozone asher device. The thermal conductivity of the support members 14 was 1950 W/m/K at 25° C.

Next, a target layer 13 having a thickness of 8 μm and a diameter of 3.5 mm was formed on one circular surface of each support member 14 by sputtering using argon as a carrier gas. An annular electrode (not shown) made of chromium was also formed on each support member 14 in a region from the periphery of the target layer 13 to the rim of the support member 14. It was confirmed that the chromium electrode extended to the side surface of the support member 14. Three multilayer targets 15 were produced by these processes.

Next, three shielding members 2 having openings formed by a mechanical process were prepared. The shielding members 2 were arranged at a pitch of 12 mm, and were integrally molded by pouring molten copper into a space around the three shielding members 2. Lastly, surfaces corresponding to the outer peripheral surfaces of the chained connection unit were mechanically ground so that the shapes thereof are adjusted. Thus, the chained connection unit 1, which is structured as illustrated in FIGS. 1A to 1C and includes the thermal transfer member 3 made of copper and the shielding members 2 made of tungsten, was prepared. The thermal conductivities of the thermal transfer member 3 and the shielding members 2 at 25° C. were 397 W/m/K and 177 W/m/K, respectively. Each shielding member 2 had a cylindrical shape and included a front shielding portion 2f and a back shielding portion 2b, each of which had a wall thickness of 2 mm.

Next, the targets 15 were coupled to the chained connection unit 1 in areas where the thermal transfer member 3 were exposed in the openings of the shielding members 2 by using the solder material 26 (not shown), as illustrated in FIG. 1B. Thus, the anode array 10 having an arrangement pitch of 12 mm was produced. The thermal conductivity of the solder material was 170 W/m/K at 25° C.

FIG. 6A is an enlarged view of a region around the connecting portion 25 between the chained connection unit 1 and each target 15 in the anode array 10 according to Example 1. As illustrated in FIG. 6A, the gap between the support member 14 and the thermal transfer member 3, which is 90 to 100 µm, is filled with the solder material 26 in a thermally conductive manner.

Next, a cathode array 12 including three electron emitting portions 11 arranged at the same pitch as the arrangement pitch of the anode array 10 was formed by fixing impregnated thermionic guns to a holder (not shown).

Next, the cathode array 12 was secured by using a jig (not shown) in an inner area 23 of an envelope 21, which was made of SUS304, and the anode array 10 was connected to an opening 22 in the envelope 21 by using silver solder (not shown). Next, the cathode array 12 and the anode array 10 were electrically connected to a current introduction terminal 34 that had been arranged in the envelope 21 in advance. The anode array 10 and the envelope 21 were electrically connected to a ground terminal 35.

Next, the inner area 23 of the envelope 21 was evacuated to vacuum by using an exhaust pipe, a vacuum pump, and a getter, all of which are not illustrated. The vacuum pressure of the envelope 21 was $2 \times 10^{-6}$ Pa.

Then, the current introduction terminal 34 was connected to a drive circuit 33. Thus, a radiation generating apparatus 20 structured as illustrated in FIG. 2A was manufactured.

Next, the driving stability of the radiation generating apparatus 20 was evaluated. The evaluation of the driving stability was performed by driving the drive circuit 33 under the following conditions. That is, the acceleration voltage was set to +100 kV, and the density of the electron current applied to the target layers 13 was set to 3 mA/mm². Pulse driving was performed by repeating an electron irradiation time of 2 seconds and a non-irradiation time of 198 seconds. The cathode array 12 was dot-sequentially driven so that the three targets 15 arranged in the arrangement direction Dat were sequentially subjected to pulse driving.

In the evaluation of stability of the radiation output intensity, the current that flows from the target layers 13 to the ground terminal 35 was measured, and control was performed using a negative feedback circuit (not shown) so that the variation in the anode current was within 1%.

The radiation output intensity was determined as the average of values obtained over a detection period of 1 second by using a radiation dosimeter placed 1 m in front of each target 15 of the anode array with a pinhole arranged therebetween. The stability was evaluated on the basis of a variation rate obtained by standardizing the radiation output intensity after 100 hours with the original radiation output intensity.

In the radiation generating apparatus 20 according to Example 1, variations in the radiation output of the targets 15 included in the anode array 10 illustrated in FIGS. 1A to 1C were 0.98, 0.99, and 0.99 in that order from the target 15 at the left.

According to the radiation generating apparatus 20 including the transmissive targets 15 of Example 1, even when the radiation generating apparatus 20 was driven for a long time, no prominent radiation output variation occurred in the arrangement direction of the array. Thus, it was confirmed that stable radiation output intensity can be obtained.

According to the anode array 10 of Example 1, the radiation output variation is suppressed because the thermal transfer member 3 is shaped so as to extend continuously in the arrangement direction Dat, and the shielding members 2 and the targets 15 are arranged discretely in the arrangement direction Dat, as illustrated in FIGS. 1A to 1C.

It was also confirmed that the radiation generating apparatus 20 was stably driven without causing a discharge in the period in which the driving stability was being evaluated.

Example 2

A radiation generating apparatus 20 of Example 2 was manufactured by a method similar to that in Example 1 except that an anode array 10 structured as illustrated in FIGS. 4A to 4C was used.

In the radiation generating apparatus 20 according to Example 2, variations in the radiation output of the targets 15 included in the anode array 10 illustrated in FIGS. 4A to 4C were 0.98, 0.98, and 0.99 in that order from the target 15 at the left.

Also in Example 2, similar to Example 1, no prominent radiation output variation occurred in the arrangement direction of the array, and it was confirmed that the radiation generating apparatus 20 was highly reliable.

Example 3

In Example 3, a radiography system 30 structured as illustrated in FIG. 8 was manufactured by using the radiation generating apparatus 20 according to Example 1.

Since the radiography system of Example 3 includes the radiation generating apparatus 20 in which the radiation output variation in the arrangement direction of the array is suppressed, X-ray images with high SN ratios were obtained.

A radiation generating apparatus according to an embodiment of the present invention includes an anode array including a plurality of shielding members for respective targets. However, the "reduction in thermal conductivity in the arrangement direction of the targets" due to the shielding members is suppressed. Thus, a high-reliability radiation generating apparatus in which the radiation output variation is suppressed and a radiography system including the radiation generating apparatus can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-025729, filed Feb. 13, 2013, which is hereby incorporated by reference herein in their entirety.

What is claimed is:
1. A radiation generating apparatus comprising:
a cathode array including a plurality of electron emitting portions; and
an anode array including a plurality of targets and a chained connection unit that connects the targets, the targets being arranged at locations corresponding to locations of the respective electron emitting portions and generating radiation when irradiated with electrons emitted from the respective electron emitting portions, wherein the chained connection unit includes a plurality of shielding members and a thermal transfer member, the shielding members being arranged at locations corresponding to the locations of the respective targets, and the thermal transfer member having a thermal conductivity higher than a thermal conductivity of the shielding members, wherein the thermal transfer member has a portion that is continuous in a direction in which the targets are arranged, wherein each target includes a target layer and a support member, the target layer generating the radiation when irradiated with the electrons emitted from the corresponding electron emitting portion, and the support member supporting the target layer, and wherein the thermal transfer member is coupled to the support members with connecting portions.

2. The radiation generating apparatus according to claim 1, wherein the shielding members have a specific gravity higher than a specific gravity of the thermal transfer member.

3. The radiation generating apparatus according to claim 1, wherein the thermal transfer member has a length greater than an arrangement length of the targets and includes a portion that is continuous in a direction in which the arrangement length is defined.

4. The radiation generating apparatus according to claim 1, wherein each connecting portion includes a side surface of the corresponding support member, a portion of the thermal transfer member, and a solder material.

5. The radiation generating apparatus according to claim 4, wherein the solder material is silver solder.

6. The radiation generating apparatus according to claim 1, wherein each of the support members has a higher thermal conductivity than that of the thermal transfer member.

7. The radiation generating apparatus according to claim 6, wherein the support members are made of diamond.

8. The radiation generating apparatus according to claim 1, wherein the targets are transmissive targets.

9. The radiation generating apparatus according to claim 1, wherein the targets are one-dimensionally arranged.

10. The radiation generating apparatus according to claim 1, wherein the shielding members contain tungsten as a main component.

11. The radiation generating apparatus according to claim 1, wherein the thermal transfer member contains copper, silver, or an alloy thereof as a main component.

12. The radiation generating apparatus according to claim 11, wherein the thermal transfer member is made of copper and the shielding members are made of tungsten.

13. The radiation generating apparatus according to claim 1, wherein the thermal transfer member is in contact with a periphery of each shielding member and surrounds the shielding member.

14. The radiation generating apparatus according to claim 1, wherein the thermal transfer member is located on a side of the targets that faces the electron emitting portions and on a side of the targets opposite to the side that faces the electron emitting portions.

15. The radiation generating apparatus according to claim 1, further comprising:
an envelope, the electron emitting portions and the target layers being arranged in an inner space or on an inner surface of the envelope.

16. The radiation generating apparatus according to claim 15, wherein the anode array is connected to the envelope.

17. The radiation generating apparatus according to claim 15, wherein the anode array is connected to an opening in the envelope and constitutes part of the envelope.

18. The radiation generating apparatus according to claim 1, further comprising:
a driving circuit that defines an anode potential and a cathode potential for the anode array and the cathode array, respectively.

19. A radiography system comprising:
the radiation generating apparatus according to claim 1;
a radiation detection apparatus that detects the radiation emitted from the radiation generating apparatus and transmitted through an object; and
a control device that controls the radiation generating apparatus and the radiation detection apparatus in association with each other.

20. A radiation generating apparatus comprising:
a cathode array including a plurality of electron emitting portions; and
an anode array including a plurality of targets and a chained connection unit that connects the targets, the targets being arranged at locations corresponding to locations of the respective electron emitting portions and generating radiation when irradiated with electrons emitted from the respective electron emitting portions,
wherein the chained connection unit includes a plurality of shielding members and a thermal transfer member, the shielding members being arranged at locations corresponding to the locations of the respective targets, and the thermal transfer member having a thermal conductivity higher than a thermal conductivity of the shielding members,
wherein the thermal transfer member has a portion that is continuous in a direction in which the targets are arranged, and
wherein the thermal transfer member is in contact with a periphery of each shielding member and surrounds the shielding member.

21. The radiation generating apparatus according to claim 20, wherein the shielding members have a specific gravity higher than a specific gravity of the thermal transfer member.

22. The radiation generating apparatus according to claim 20, wherein the thermal transfer member has a length greater than an arrangement length of the targets and includes a portion that is continuous in a direction in which the arrangement length is defined.

23. The radiation generating apparatus according to claim 20,
wherein each target includes a target layer and a support member, the target layer generating the radiation when irradiated with the electrons emitted from the corresponding electron emitting portion, and the support member supporting the target layer,
wherein the thermal transfer member is coupled to the support members with connecting portions, and
wherein each connecting portion includes a side surface of the corresponding support member, a portion of the thermal transfer member, and a solder material.

24. The radiation generating apparatus according to claim 23, wherein the solder material is silver solder.

25. The radiation generating apparatus according to claim 20,
wherein each target includes a target layer and a support member, the target layer generating the radiation when irradiated with the electrons emitted from the corresponding electron emitting portion, and the support member supporting the target layer, wherein the thermal transfer member is coupled to the support members with connecting portions, and wherein each of the support members has a higher thermal conductivity than that of the thermal transfer member.

26. The radiation generating apparatus according to claim 25, wherein the support members are made of diamond.

27. The radiation generating apparatus according to claim 20, wherein the targets are transmissive targets.

28. The radiation generating apparatus according to claim 20, wherein the targets are one-dimensionally arranged.

29. The radiation generating apparatus according to claim 20, wherein the shielding members contain tungsten as a main component.

30. The radiation generating apparatus according to claim 20, wherein the thermal transfer member contains copper, silver, or an alloy thereof as a main component.

31. The radiation generating apparatus according to claim 30, wherein the thermal transfer member is made of copper and the shielding members are made of tungsten.

32. The radiation generating apparatus according to claim 20, wherein the thermal transfer member is located on a side of the targets that faces the electron emitting portions and on a side of the targets opposite to the side that faces the electron emitting portions.

33. The radiation generating apparatus according to claim 20, further comprising:
an envelope, the electron emitting portions and the target layers being arranged in an inner space or on an inner surface of the envelope.

34. The radiation generating apparatus according to claim 33, wherein the anode array is connected to the envelope.

35. The radiation generating apparatus according to claim 33, wherein the anode array is connected to an opening in the envelope and constitutes part of the envelope.

36. The radiation generating apparatus according to claim 20, further comprising:
a driving circuit that defines an anode potential and a cathode potential for the anode array and the cathode array, respectively.

37. A radiography system comprising:
the radiation generating apparatus according to claim 20;
a radiation detection apparatus that detects the radiation emitted from the radiation generating apparatus and transmitted through an object; and
a control device that controls the radiation generating apparatus and the radiation detection apparatus in association with each other.

38. A radiation generating apparatus comprising:
a cathode array including a plurality of electron emitting portions; and
an anode array including a plurality of targets and a chained connection unit that connects the targets, the targets being arranged at locations corresponding to locations of the respective electron emitting portions and generating radiation when irradiated with electrons emitted from the respective electron emitting portions,
wherein the chained connection unit includes a plurality of shielding members and a thermal transfer member, the shielding members being arranged at locations corresponding to the locations of the respective targets, and the thermal transfer member having a thermal conductivity higher than a thermal conductivity of the shielding members,
wherein the thermal transfer member has a portion that is continuous in a direction in which the targets are arranged, and wherein the thermal transfer member is located on a side of the targets that faces the electron emitting portions and on a side of the targets opposite to the side that faces the electron emitting portions.

39. The radiation generating apparatus according to claim 38, wherein the shielding members have a specific gravity higher than a specific gravity of the thermal transfer member.

40. The radiation generating apparatus according to claim 38, wherein the thermal transfer member has a length greater than an arrangement length of the targets and includes a portion that is continuous in a direction in which the arrangement length is defined.

41. The radiation generating apparatus according to claim 38,
wherein each target includes a target layer and a support member, the target layer generating the radiation when irradiated with the electrons emitted from the corresponding electron emitting portion, and the support member supporting the target layer,
wherein the thermal transfer member is coupled to the support members with connecting portions, and
wherein each connecting portion includes a side surface of the corresponding support member, a portion of the thermal transfer member, and a solder material.

42. The radiation generating apparatus according to claim 41, wherein the solder material is silver solder.

43. The radiation generating apparatus according to claim 38,
wherein each target includes a target layer and a support member, the target layer generating the radiation when irradiated with the electrons emitted from the corresponding electron emitting portion, and the support member supporting the target layer,
wherein the thermal transfer member is coupled to the support members with connecting portions, and
wherein each of the support members has a higher thermal conductivity than that of the thermal transfer member.

44. The radiation generating apparatus according to claim 43, wherein the support members are made of diamond.

45. The radiation generating apparatus according to claim 38, wherein the targets are transmissive targets.

46. The radiation generating apparatus according to claim 38, wherein the targets are one-dimensionally arranged.

47. The radiation generating apparatus according to claim 38, wherein the shielding members contain tungsten as a main component.

48. The radiation generating apparatus according to claim 38, wherein the thermal transfer member contains copper, silver, or an alloy thereof as a main component.

49. The radiation generating apparatus according to claim 38, wherein the thermal transfer member is made of copper and the shielding members are made of tungsten.

50. The radiation generating apparatus according to claim 38, further comprising:
an envelope, the electron emitting portions and the target layers being arranged in an inner space or on an inner surface of the envelope.

51. The radiation generating apparatus according to claim 50, wherein the anode array is connected to the envelope.

52. The radiation generating apparatus according to claim 50, wherein the anode array is connected to an opening in the envelope and constitutes part of the envelope.

53. The radiation generating apparatus according to claim 38, further comprising:
a driving circuit that defines an anode potential and a cathode potential for the anode array and the cathode array, respectively.

54. A radiography system comprising:
the radiation generating apparatus according to claim 38;
a radiation detection apparatus that detects the radiation emitted from the radiation generating apparatus and transmitted through an object; and
a control device that controls the radiation generating apparatus and the radiation detection apparatus in association with each other.

* * * * *